United States Patent
Wang

(10) Patent No.: US 9,846,940 B1
(45) Date of Patent: Dec. 19, 2017

(54) SPECTRALLY ENCODED ENDOSCOPIC IMAGE PROCESS

(71) Applicant: Canon U.S.A. Inc., Melville, NY (US)

(72) Inventor: Zhuo Wang, Middleton, MA (US)

(73) Assignee: CANON U.S.A., INC., Melville, NY (US)

( * ) Notice: Subject to any disclaimer, the term of this patent is extended or adjusted under 35 U.S.C. 154(b) by 0 days.

(21) Appl. No.: 15/237,241

(22) Filed: Aug. 15, 2016

(51) Int. Cl.
| G06K 9/32 | (2006.01) |
| G06T 7/00 | (2017.01) |
| G06T 3/00 | (2006.01) |
| G06T 5/00 | (2006.01) |
| G01J 3/28 | (2006.01) |
| H04N 5/225 | (2006.01) |

(52) U.S. Cl.
CPC .......... *G06T 7/0018* (2013.01); *G01J 3/2823* (2013.01); *G06T 3/0006* (2013.01); *G06T 5/006* (2013.01); *G06T 2207/10068* (2013.01); *H04N 5/225* (2013.01); *H04N 2005/2255* (2013.01)

(58) Field of Classification Search
CPC .................. G06T 3/0006; G06T 5/006; G06T 2207/10068; G01J 3/2823
See application file for complete search history.

(56) References Cited

U.S. PATENT DOCUMENTS

| 6,346,940 B1 | 2/2002 | Fukunaga |
| 7,546,156 B2 | 6/2009 | Madden et al. |
| 8,045,780 B2 | 10/2011 | Boese et al. |
| 8,675,935 B2 | 3/2014 | Higgins et al. |

(Continued)

FOREIGN PATENT DOCUMENTS

| EP | 0 908 849 A1 | 4/1999 |
| WO | 02/38040 A2 | 5/2002 |
| WO | 2015149041 A1 | 10/2015 |

OTHER PUBLICATIONS

Nehama, S, et al, "Spectral Imaging Using Spectrally Encoded Endoscopy", Abstract 2015 from website http://www.bm.technion.ac.il/¬ SiteCollectionDocuments/-ProjectAbstracts2015.pdf.

(Continued)

*Primary Examiner* — Phuoc Tran
(74) *Attorney, Agent, or Firm* — Canon U.S.A., Inc., IP Division

(57) ABSTRACT

An image processing method. At least one light ray presented by a vector in a first affine coordinate system with a tip of the probe as an origin is projected from the tip of the probe. The light ray is intercepted from a projection surface satisfying a function in the first affine coordinate. A distance between the tip of the probe and an interception point of the light ray on the projection surface is obtained based on a rotation angle of the probe, a wavelength of the light ray, and a deflection angle of the light ray from the probe. A relationship between the first coordinate and a second affine coordinate system defined with the projection surface as a reference is obtained. Image data are acquired from the light ray reflected from the target surface presented in the first affine coordinate. The image data presented in the first affine coordinate are converted into image data presented in the second affine coordinate, and the image data in the second coordinate system are resampled by interpolating or extrapolating a gray scale.

32 Claims, 10 Drawing Sheets

(56) References Cited

U.S. PATENT DOCUMENTS

| | | |
|---|---|---|
| 9,138,597 B2 | 9/2015 | Weersink et al. |
| 2004/0222987 A1* | 11/2004 | Chang ................ G01B 11/2509 345/419 |
| 2006/0017720 A1* | 1/2006 | Li ...................... G01B 11/2504 345/419 |
| 2012/0190928 A1 | 7/2012 | Boudoux et al. |
| 2013/0093867 A1* | 4/2013 | Schick ............... A61B 1/00167 348/65 |
| 2014/0376821 A1 | 12/2014 | Meir et al. |
| 2016/0065915 A1 | 3/2016 | Potter et al. |

OTHER PUBLICATIONS

Risi, M., et al, "Analysis of multimode fiber bundles for endoscopic spectral-domain optical coherence tomography", Applied Optics, Jan. 1, 2015, pp. 101-113, vol. 54, No. 1.

Zeidan, A., et al, "Spectral imaging using forward-viewing spectrally encoded endoscopy", Biomedical Optics Express, Feb. 1, 2016, pp. 392-398, vol. 7, No. 2.

Zeidan, A., et al, "Minature forward-viewing spectrally encoded endoscopic probe", Optics Letter, Aug. 15, 2014, pp. 4871-4874, vol. 39, No. 16.

\* cited by examiner

SPECTRALLY ENCODED ENDOSCOPIC IMAGE PROCESS

BACKGROUND

Field of the Disclosure

The present disclosure relates in general to a spectrally encoded endoscope (SEE), and more particularly, to image rectification and image registration of image data acquired by the spectrally encoded endoscope.

Description of the Related Art

The first endoscope was invented more than 50 years ago and consisted of a bundle of optical fibers. Since then, significant progress in minimally invasive surgeries and thereby reducing the risk of complications, costs, and recovery times has been made.

With the advent of inexpensive and miniature CMOS sensors which are mainly used in smart phones, endoscopes are shifting from fiber bundles into designs with imaging sensors at the distal tip of a probe. One significant drawback on these CMOS sensor based endoscopes is the tradeoff between the scope diameter and the resolution. The spectrally encoded endoscope (SEE) is one of the smallest endoscope that has shown a great potential for the use in minimally invasive surgeries; however, the images of target obtained by SEE probes suffer from distortion in a two-dimensional view. Therefore, to obtain an accurate investigation of a target while maintaining the minimal invasive characteristics provided by the SEE probes, the distortion issue has to be resolved.

SUMMARY

According to aspect of the invention, an image processing method for a spectrally encoded endoscope is provided. At least one light ray is projected from a probe. The light ray is presented by a vector in a first affine coordinate system with a tip of the probe, more specifically, the geometric center of the light covered area on the grating surface at the tip, as an origin. The light ray is intercepted with a projection surface which satisfies a function in the first affine coordinate system. A distance between the tip of the probe and an interception point of the light ray on the projection surface is obtained based on a rotation angle of the probe, a wavelength of the light ray, and a deflection angle of the light ray from the probe. A relationship between the first coordinate and a second affine coordinate system is obtained, while the second coordinate system is defined with the projection surface as a reference. Image data is acquired from the light ray reflected from the target surface presented in the first affine coordinate. The image data presented in the first affine coordinate is then converted into image data presented in the second affine coordinate. The image data is then resampled in the second coordinate system by interpolating or extrapolating a gray scale.

In one embodiment, the first coordinate may include a Cartesian coordinate including an x-axis, a y-axis, and a z-axis extending along the probe, such that the vector of the light ray may be presented as:

$$\begin{cases} x = r\sin\theta\cos\varphi \\ y = r\sin\theta\sin\varphi \\ z = r\cos\theta \end{cases},$$

where r is the length of the light ray, $\theta$ is the deflection angle of the light ray, and $\varphi$ is an azimuth angle of the light ray. The function of the target plane satisfies $f(x, y, z)=0$ at the interception point between the light ray and the projection plane. The azimuth angle $\varphi$ may be determined based on a series of rotation angles of the probe with respect to scanning time between the rotation angles in a calibration or mapping process; the wavelength of the light ray $\lambda$ may be determined based on interpolation or extrapolation from at least two distinct wavelengths and their corresponding pixel indices of pixels configured to receive the reflected light ray; and the deflection angle $\theta$ may be determined based on the wavelength of the light ray $\lambda$, the light incident angle on the grating, the grating constant, the diffraction order, and refractive indices at two opposing sides of the grating.

In one embodiment, the second affine coordinate system may also include a Cartesian coordinate system. The projection plane may be a target surface to be imaged and analyzed. Alternatively, the projection plane is separate from a target surface to be imaged and analyzed. When being a separate plane from the target surface, the projection plane may include a conjugate plane of a hypothetical image plane of the target surface to be imaged and analyzed.

In one embodiment, multiple light rays may be projected from the tip of the probe onto the projection plane. A grayscale value may be interpolated to resample the image data presented in the second affine coordinate.

According to another aspect of the invention, an image processing method comprising the following steps is provided: a) projecting at least one light ray of a first color from a probe, wherein the light ray is presented by a vector in a first affine coordinate system with a tip of the probe as an origin; b) intercepting the light ray with a projection plane, the projection plane satisfying a function in the first affine coordinate; c) obtaining a distance between the tip of the probe and an interception point of the light ray and the projection plane based on a rotation angle of the probe, a wavelength of the light ray, and a deflection angle of the light ray from the probe; d) obtaining a relationship between the first coordinate and a second affine coordinate system, the second coordinate system being defined with the projection plane as a reference; e) acquiring image data from the light ray reflected from the target plane presented in the first affine coordinate; f) converting the image data presented in the first affine coordinate into image data presented in the second affine coordinate; g) repeating steps a) to f) for a light ray of second and third colors; h) overlaying the image data acquired from the light rays of the first, second, and third colors; and i) resampling the overlaid image by interpolating or extrapolating the image data presented in the second affine coordinate.

According to another aspect of the invention, a spectrally encoded endoscopic apparatus is provided. The apparatus comprises a light source; a probe having a proximal end optically coupled to the light source and a distal end; a grating attached to the distal end; and a spectrometer. The light source is configured to generate a light propagating through the grating, intercepting with an object surface in a three dimension, and then project onto a projection plane. The spectrometer is configured to receive the light reflected from the 3-dimensional object surface and hence the projection plane; obtain location information of image data carried by the reflected light presented in a first coordinate system with reference to the probe based on a rotation angle of the probe, a wavelength of the light, and a deflection angle of the light deflecting from the probe; transform the location information of the image data from the first coordinate system into a second coordinate system with reference to the projection plane; and resample the image data by interpolating or extrapolating a grayscale value.

The apparatus may further comprises a galvo motor or a motor configured to rotate the probe; a processor, and an encoder configured to control and calibrate the galvo motor or the motor, so as to determine the rotation angle of the probe. The projection plane may include a target surface to be imaged and analyzed by the spectrometer. Alternatively, the projection plane may be separate from a target surface to be imaged and analyzed by the spectrometer, and the spectrometer is further configured to generate a perspective view or a fisheye view of the image data in accordance with an angle and a distance of the projection plane with respect to the probe.

DETAILED DESCRIPTION

The following description is of certain illustrative embodiments, although other embodiments may include alternatives, equivalents, and modifications. Additionally, the illustrative embodiments may include several novel features, and a particular feature may not be essential to practice the devices, systems, and methods described herein.

Figure 1:
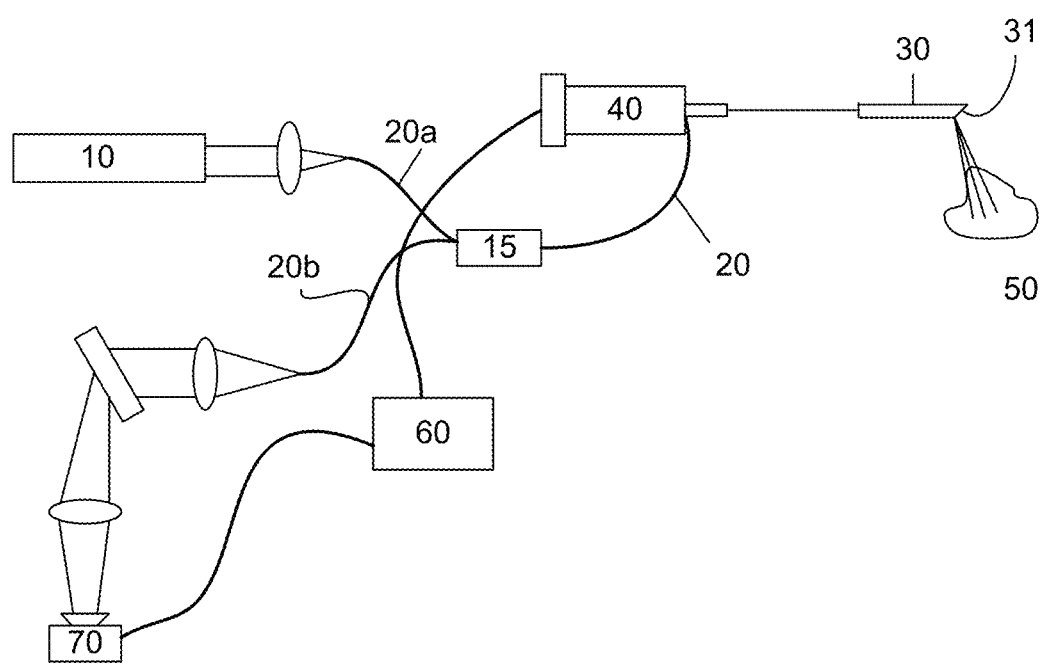
FIG. 1 is a schematic drawing of a spectrally encoded endoscopic (SEE) system and a probe according to one embodiment of this invention.

FIG. 1 shows a schematic drawing of a spectrally encoded endoscopic (SEE) apparatus. The SEE apparatus includes a light source 10, preferably a broadband light source such as a supercontinuum laser coupled with a proximal end of a fiber 20a, preferably single mode fiber (SMF). The distal end of the fiber 20a is attached with an SEE probe 30. The SEE probe 30 is preferably formed by attaching the fiber 20a to a focusing element (not shown) to form a spot several millimeters away from a tip of the probe 30. The distal end of the SEE probe 30 includes a grating 31 to disperse the broadband light spot into a rainbow line. The sample is scanned orthogonal to the wavelength axis by rotating the SEE probe 30. As shown in FIG. 1, the rotation of the SEE probe 30 is controlled by a galvo motor 40. The diffracted light from the grating 31 is then incident on a target plane 50. The light reflected from the target plane P may be collected by another fiber 20b, for example, a multimode fiber. Three-dimensional information of image data of the target plane 50 carried by the light reflected from the target plane 50 is then analyzed by the spectrometer 70. A computer 60 may control and acquire data from the spectrometer and control the motor 40. The three-dimensional information includes the location, angle, and shape of a target to be imaged. In one embodiment, the fiber 20b to collect the light reflected from the target plane 50 may be coupled with the fiber 20a for transmitting light from the light source 10 into the fiber bundle 20 by a coupler 15 as shown in FIG. 1. If a non-oscillating motor is used instead, a rotary junction (not shown) is needed to connect the light source 10 or spectrometer 70 or both to the probe 30.

Due to its smaller diameter of about hundred microns, the probe 30 is flexible and can be maneuvered to inspect hard-to-reach areas with a minimum bending radius of several millimeters. Other color lights and fluorescent light can also be used as the light source for the SEE apparatus. The SEE apparatus as shown in FIG. 1 provides image rectification as a transformation process used to project light onto a designated plane. Once the projection is done, it is possible to display the image data of the reflected light of the projection in different views. The image registration is defined as the process of transforming different sets of image data into one coordinate system. The processes of image rectification and registration will be described in details as follows.

Figure 2:
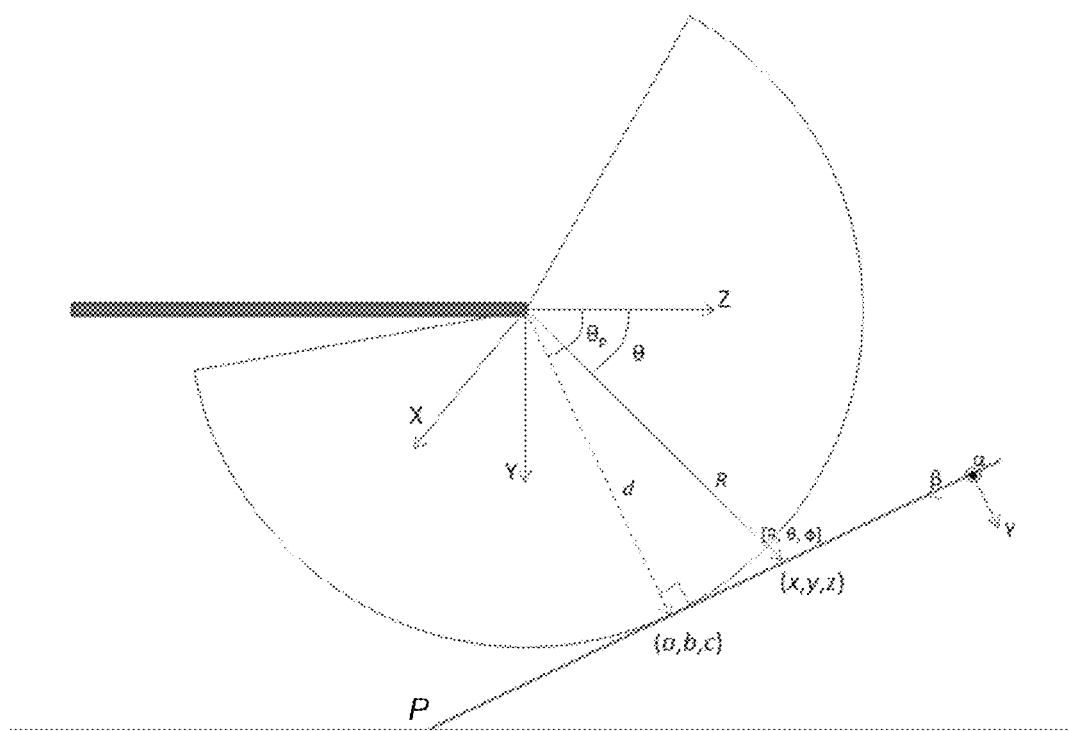
FIG. 2 shows the propagating path of the light projected from the probe of the SEE system as illustrated in FIG. 1.

Image rectification is an image transformation process used to project one or more images onto a designated image plane. As shown in FIG. 2, the light source 10 generates a light traveling through the fiber 20a and the SEE probe 30. The light is then diffracted by the grating 31 and incident on a target plane, for example, the target plane P as shown in FIG. 2. The propagation path of the light may be presented by a vector in a three-dimensional affine coordinate system. In the embodiment as shown in FIG. 2, a Cartesian coordinate system is selected with the tip of the probe 30 as the origin and the rotation axis of the probe 30 defined as the z-axis. The light projecting from the tip of the probe 30 may be presented by a vector in a three-dimensional coordinate system as Equation (1):

$$\begin{cases} x = r\sin\theta\cos\varphi \\ y = r\sin\theta\sin\varphi \\ z = r\cos\theta \end{cases} \quad (1)$$

where r is the length of the light ray, θ is the deflection angle of the light ray with respect to the z-axis, and φ is the azimuth angle, which is measured from the angle between x-axis and the projection of the light ray on the XY plane. In general, the target plane P can be presented by a function of x, y, and z, that is, $$f(x,y,z)=0 \quad (2).$$

From Equations (1) and (2), the length of the light ray, that is, the distance between the tip and the interception point of the light ray and the target plane r can be solved and thus the interception point of each light ray in the three-dimension is determined. This is evident if one considers a plane in the three-dimension of the interception point (x,y,z) satisfies:

$$(a, b, c)\begin{pmatrix} x-a \\ y-b \\ z-c \end{pmatrix} = 0 \quad (3)$$

where (a, b, c) is the surface normal of the plane as shown in FIG. 2. It is not unlikely that the light ray may intercept with a three-dimensional target plane multiple times. In such situation, the smallest positive r is preferably selected as the interception point of the light ray and the target plane P.

Figure 3:
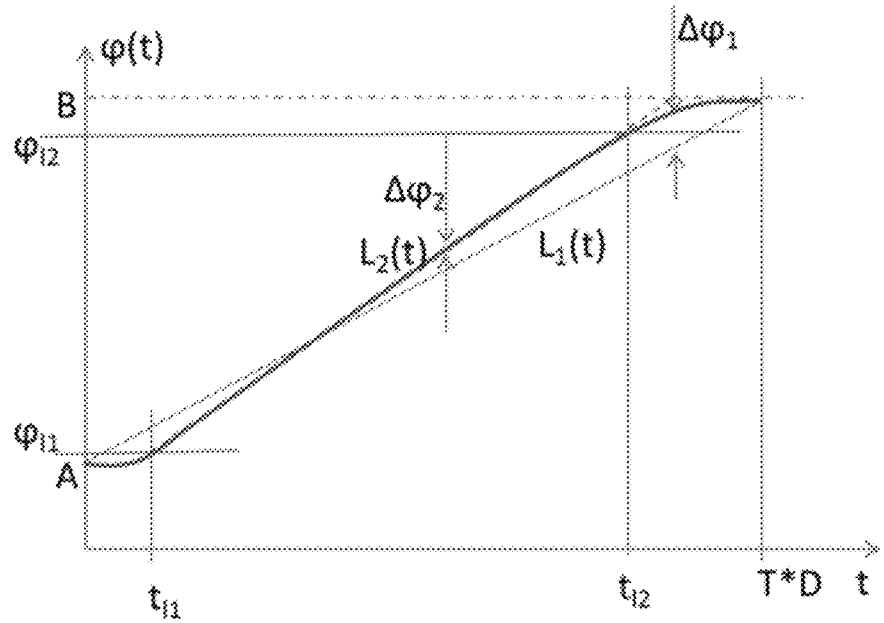
FIG. 3 is a graph showing the displacement curve of an oscillation motor driving the probe.

As discussed above, the probe 30 rotates about the z-axis. The azimuth angle φ can be determined by an encoder of a motor driving the probe, for example, the galvo motor 40 as shown in FIG. 1. The motor may be controlled by a processor such as a personal computer 60 as shown in FIG. 1. FIG. 3 shows a displacement curve of an oscillator motor that satisfies dφ(t)/dt≈0 at time $t_1$ (A) and time $t_2$ (B). The slope of the curve between A and B is close to a constant v. The real steps of the motor are presented by the solid line, while the ideal steps of the motor are presented by the dashed line in FIG. 3. Calibration may be needed to determine the relationship between the real scanning steps and the ideal scanning steps of the rotation of the probe. When the curve is linear, the scanning steps $\phi_m$ satisfies:

$$\varphi_m = \frac{\Gamma}{N}\left(m - \frac{N}{2}\right) \tag{4}$$

where Γ is the total scanning angle, for example, 70° in one embodiment of the current invention, N is the number of linear portion of pixels, for example, 800 and m is the step index between 1 and N.

Alternatively, it might be preferable to include an encoder to motor to record the curve as shown in FIG. 3, that is, what the rotation angle of the motor will be at a specific time. It also may be preferred to have a continuous rotation rather than oscillation for many applications.

Figure 4:
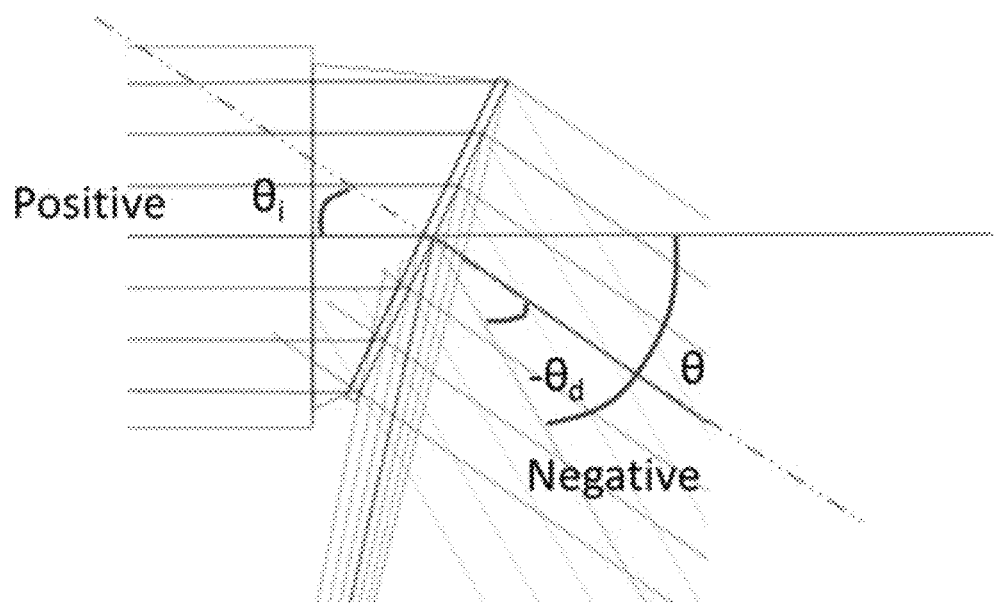
FIG. 4 shows the relationship between the incident angle, the diffractive angle, and the deflection angle of a light ray propagating through the grating as shown in FIG. 1.

Each wavelength of the light propagating through the grating 31 is diffracted to a distinct angle towards the target plane. Equation (5) shows the relationship between the spectral distribution of the light ray projected from the probe 30 and the incident angle and the diffractive angle of the light propagating through grating 31:

$$n_i \sin \theta_i + n_d \sin \theta_d = lG\lambda \tag{5}$$

where $n_i$ and $n_d$ are the refractive indices of the media through which the light propagates, including the incident side and the diffractive side of the grating 31, respectively; $\theta_i$ is the incident angle of the light onto the grating 31; $\theta_d$ is the diffractive angle of the light projecting from the grating 31; l is the diffraction order, G is the grating constant of the grating 31, and λ is the wavelength of the light. Further, as shown in FIG. 4, the deflection angle θ as a function of the wavelength of the light satisfies the Equation (6) as:

$$\theta(\lambda) = \theta_i - \theta_d(\lambda) \tag{6}$$

Figure 5:
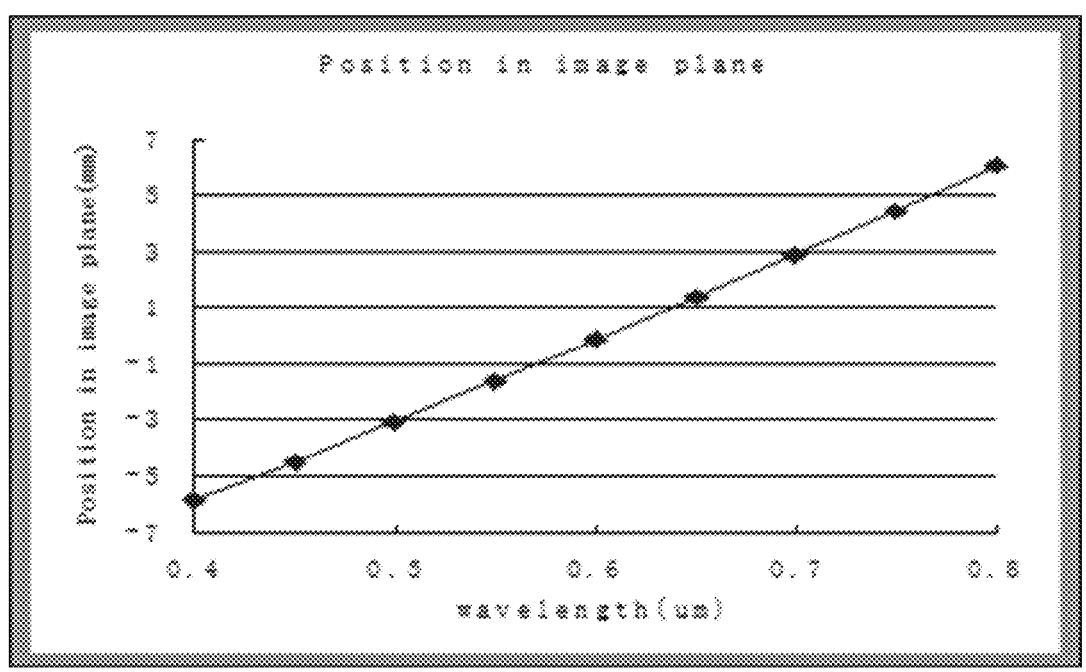
FIG. 5 shows the spectral distribution of the light at the spectrometer.

The wavelength λ of the light at the spectrometer may be calibrated based on interpolation or extrapolations from two or more wavelengths, that is, two or more color lights, and the pixel index P(λ) of each pixel by Equation (7):

$$\lambda = \frac{\lambda_2 - \lambda_1}{P(\lambda_2) - P(\lambda_1)}[P(\lambda) - P(\lambda_1)] + \lambda_1 \tag{7}$$

where $\lambda_1$ and $\lambda_2$ are the wavelengths of known spectra, for example, blue and red lasers. The linearity of the spectral distribution at the spectrometer is shown in FIG. 5. In another embodiment, three reference wavelengths, for example, blue, red, and green lasers, or even more reference wavelengths, can be applied to a polynomial for correcting the wavelength of the collected light.

By applying the deflection angle θ and the azimuth angle φ obtained from Equations (4) and (6), the distance between the tip of the probe 30 and the coordinate of the interception point (x, y, z) can be obtained. With the information derived from the light reflected from the target plane P, the image data of the target plane P can be analyzed at the spectrometer 70 and the image of the target plane P can be presented in the coordinate with the tip of the probe 30. However, as the image (image data) is presented in the coordinate with the tip of the probe as the origin, distortion and deviation can be expected from the actual image presented in the coordinate of the target plane P itself. Therefore, the image data presented in the coordinate of (x, y, z) are resampled into a coordinate system of (α, β, γ) of the target plane P as follows. The coordinate system having its origin on the target plane P can be any Affine coordinate, Cartesian or non-Cartesian. When an affine coordinate system is selected, a transformation between the coordinate system with reference to the probe and the coordinate system of or with reference to the target plane P can be presented as:

$$\begin{pmatrix} x \\ y \\ z \end{pmatrix} = C \begin{pmatrix} \alpha \\ \beta \\ \gamma \end{pmatrix} + \begin{pmatrix} x_0 \\ y_0 \\ z_0 \end{pmatrix} \tag{8}$$

where C is the transition matrix between the coordinate system of (x, y, z) and the new coordinate system of (α, β, γ) as:

$$C = \begin{bmatrix} C_{11} & C_{12} & C_{13} \\ C_{21} & C_{22} & C_{23} \\ C_{31} & C_{32} & C_{33} \end{bmatrix}$$

and ($x_0$, $y_0$, $z_0$) is the original of the new coordinate system. The transition matrix C can be derived from Equation (9):

$$(\vec{\alpha}, \vec{\beta}, \vec{\gamma}) = (\vec{x}, \vec{y}, \vec{z}) \begin{bmatrix} C_{11} & C_{12} & C_{13} \\ C_{21} & C_{22} & C_{23} \\ C_{31} & C_{32} & C_{33} \end{bmatrix} \tag{9}$$

In the situation where the target plane 50 is a plane normal of (0, b, c), the surface of the target plane 50 can be presented as:

$$(0, b, c) \begin{pmatrix} x \\ y - b \\ z - c \end{pmatrix} = 0 \tag{10}$$

From Equations (1) and (10), the length of the light ray r can be solved as:

$$r = \frac{d^2}{b\sin\theta\sin\varphi + c\cos\theta} \tag{11}$$

Equation (8) can be modified as:

$$\begin{pmatrix} x \\ y \\ z \end{pmatrix} = C \begin{pmatrix} \alpha \\ \beta \\ \gamma \end{pmatrix} + \begin{pmatrix} 0 \\ b \\ c \end{pmatrix} \quad (12)$$

The relationship between these two coordinate systems can be presented by Equation (13):

$$(\vec{\alpha}, \vec{\beta}, \vec{\gamma}) = (\vec{x}, \vec{y}, \vec{z}) \begin{bmatrix} 1 & 0 & 0 \\ 0 & \cos\theta_p & \sin\theta_p \\ 0 & -\sin\theta_p & \cos\theta_p \end{bmatrix} = (\vec{x}, \vec{y}, \vec{z}) C \quad (13)$$

where $$\sin\theta_p = \frac{b}{d}$$

and $$\cos\theta_p = \frac{c}{d}.$$

According to Equation (11), the coordinate transformation between the coordinate systems of $(\alpha, \beta, \gamma)$ and $(x, y, z)$ satisfies:

$$\begin{pmatrix} \alpha \\ \beta \\ \gamma \end{pmatrix} = \begin{bmatrix} 1 & 0 & 0 \\ 0 & \cos\theta_p & \sin\theta_p \\ 0 & -\sin\theta_p & \cos\theta_p \end{bmatrix} \begin{pmatrix} x \\ y-b \\ z-c \end{pmatrix} = \begin{pmatrix} x \\ \frac{c(y-b)-b(z-c)}{d} \\ 0 \end{pmatrix} \quad (14)$$

Figure 6:
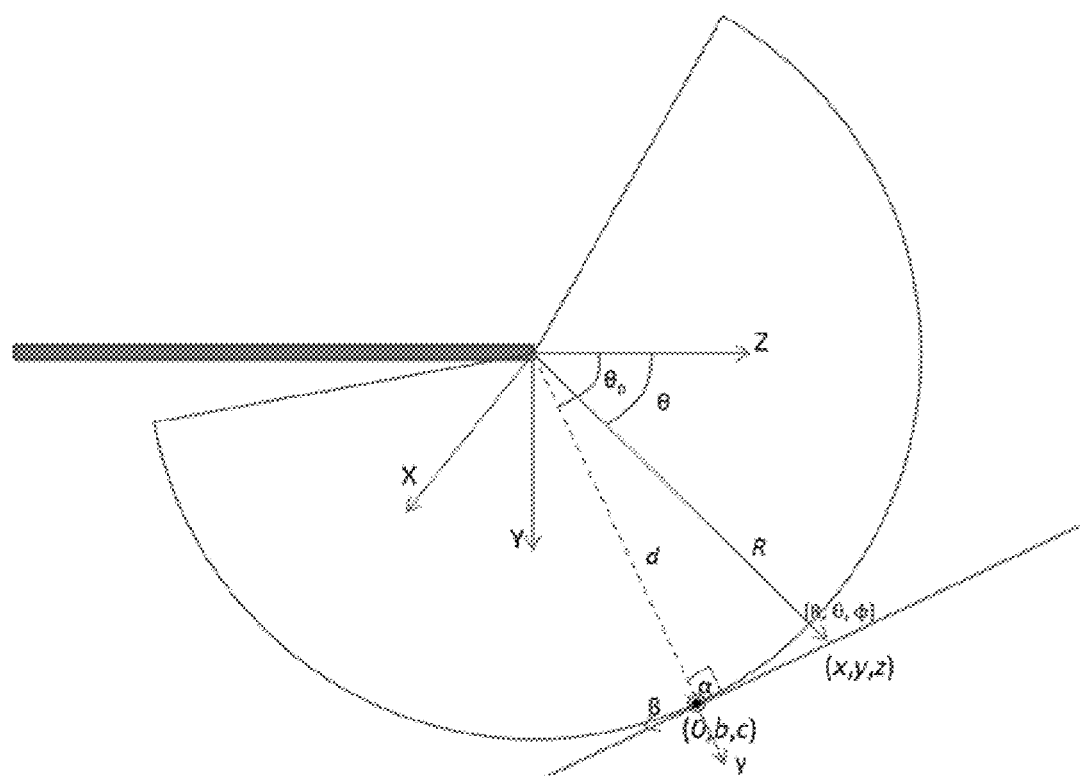
FIG. 6 shows the propagation path of the light in a three-dimensional SEE system when the target plane is a plane normal of (0, b, c)

As shown in FIG. 6, the deflection angle θ can be solved by Equation (6), where the diffractive angle $\theta_d$ is a function of the wavelength λ of the diffractive light ray. For a forward-view application, $\theta_p=0$ and thus b=0, c=d, the solution is simplified as:

$$\begin{pmatrix} \alpha \\ \beta \\ \gamma \end{pmatrix} = \begin{pmatrix} x \\ y \\ 0 \end{pmatrix} \quad (15)$$

In this situation, no coordinate transformation is needed from (x, y, z) to (α, β, γ) is needed. It is possible to derive from the spherical coordinate [R, θ, ϕ] to Cartesian (x, y, z) and resample the plane (x,y).

Figure 7:
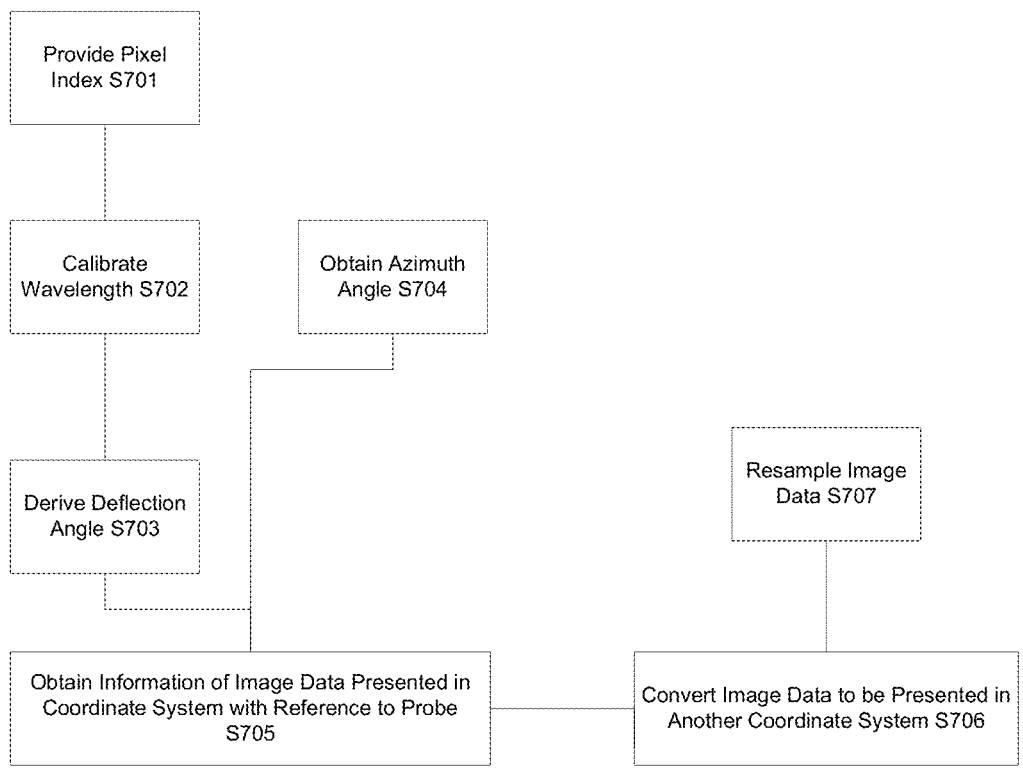
FIG. 7 shows the process flow of an image rectification method according to one embodiment of this invention.

FIG. 7 shows the process flow of the image rectification as discussed above. Assuming the SEE apparatus includes a number of pixels, for example, 1024 pixels, for receiving the image of the target plane carried by the light reflected from the target plane. The pixel index of each of the 1024 pixels is denoted as $P_n(\lambda)$, where n=1 to 1024 in step S701. In step S702, the wavelength λ of each light ray incident on each pixel is calibrated based on the pixel index $P_n(\lambda)$ of the specific pixel n as Equation (7). The deflection angle θ is derived as a function of the calibrated wavelength λ from Equations (5) and (6) in step S703. The azimuth angle ϕ can be derived based on the rotation angle of the probe presented in Equation (4) in step S704. In step S704, the deflection angle θ and the azimuth angle ϕ obtained in steps S703 and S704 is applied to Equations (1) and (2) to derive the distance R between the tip of the probe and the target plane. Steps S701 to S704 provide information of image data of the target plane in the coordinate system with reference to the probe. That is, the image of the target plane is presented in the coordinate system with reference to the probe. In step S705, information of image data presented in the coordinate system with reference to the probe is obtained. A mapping is thus established as $g(P_n, m) \rightarrow g(x,y,z)$, where g is the grayscale value. In step 706, a transformation matrix C between the coordinate system with reference to the probe and a coordinate system with reference to the target plane is obtained. The image data is then converted based on the transformation and presented by the coordinate system with reference to the target plane in this step afterwards. The image data presented in the coordinate system with reference to the target plane are then resampled by interpolation or extrapolation for proper display in step S707.

The above computation and visualization of the image of the target plane can be done by parallel computing or GPU computing for faster processing and display.

In additional to the planar surface, the target may have a surface with more complex shapes such as a quadratic surface as:

$$ax^2+by^2+cz^2+2fyz+2gzx+2hxy+2px+2qy+2rz+d=0 \quad (16)$$

where a, b, c, f, g, h, p, q, r, d are known parameters related to the quadratic surface. In general, the surface can be presented as:

$$\Sigma_{i_x=0}^{N_x} \Sigma_{i_y=0}^{N_y} \Sigma_{i_z=0}^{N_z} a_{i_x} a_{i_y} a_{i_z} x^{i_x} y^{i_y} z^{i_z}=0 \quad (17)$$

where $a_{i_x i_y i_z}$ is the known coefficient related to the higher order surface of the target. Depending on the target to be imaged, the three-dimensional surface can take any form of interest.

Figure 8:
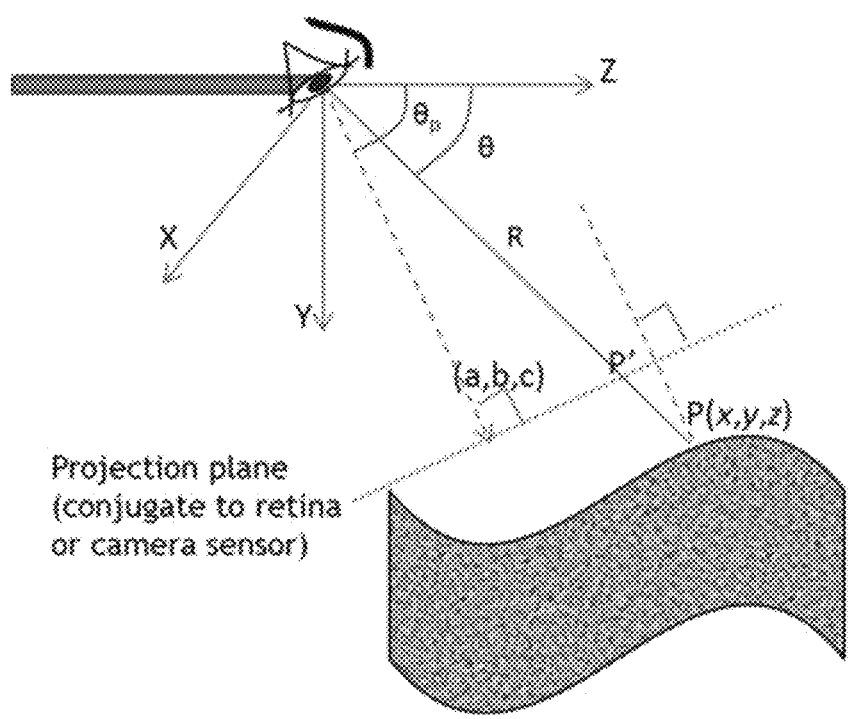
FIG. 8 shows the propagation path of light in a perspective view application of the SEE system.
Figure 9:
FIG. 9 shows a fisheye view.

In the embodiment discussed above, it is assumed that the target plane overlaps with the surface of a target object to be imaged and analyzed. In the situation that the surface of the target object is curved or even irregularly shaped, the target plane may be separate from the surface of the target object as shown in FIG. 8. In FIG. 8, considering a human eye ball is placed at the tip of the probe 30 or the camera sensor if a CMOS camera is placed, the solution of the interception point P(x,y,z) on the surface of the target object can be projected to a projection plane P' to obtain perspective view of the target surface P. The perspective view provides the depth perception to the observer, i.e., the closer object will appear bigger. The projection plane is a plane conjugate to the retina of the human eyeball or the camera sensor. It is even possible to construct other types of views if the projection plane is a curved surface as discussed in Equations (16) and (17). One specific such application includes a wide angle camera lens, for example, a fisheye lens as shown in FIG. 9.

Figure 10:
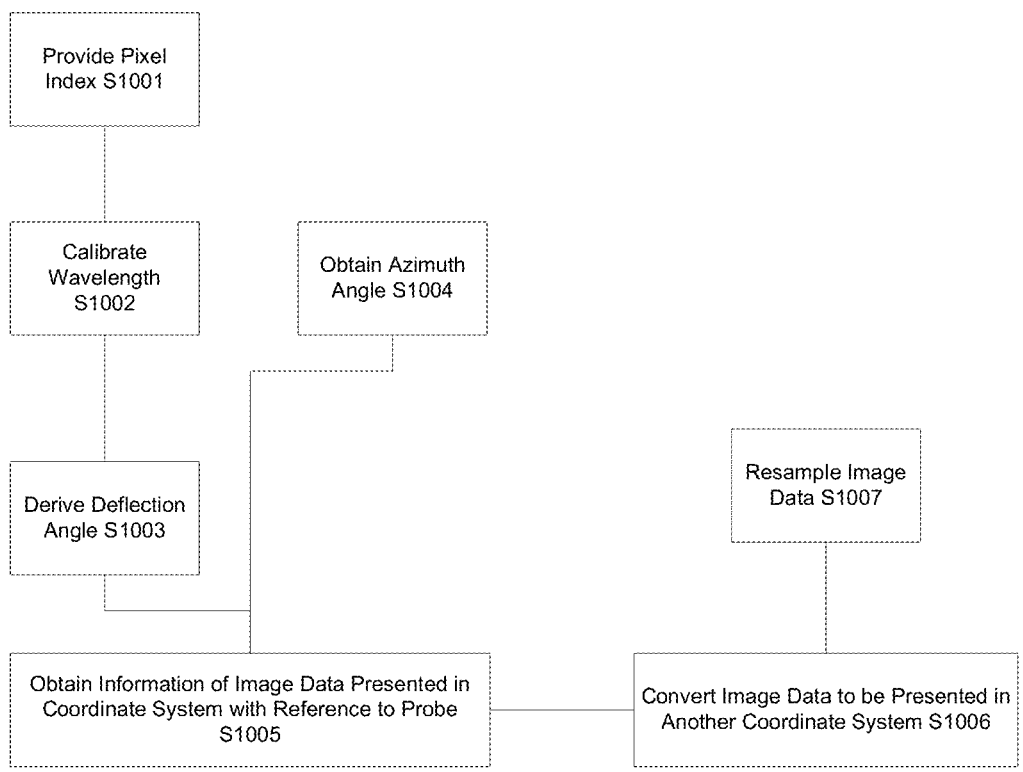
FIG. 10 is a flow chart of the perspective view application of the SEE system.

The image rectification process for the perspective view application is similar to those as described in FIG. 7. However, different from the process in FIG. 7, the function of the projection plane P' is predetermined, and the interception point P'(x,y,z) is to be derived. As shown in FIG. 10, in step 1001, a plurality of pixels, for example, 1024 pixels, for receiving the image data of the projection plane P' is provided. The pixel index of each of the pixels is also provided in step 1001. The pixel index of each of the 1024 pixels is denoted as $P_n(\lambda)$, where n=1 to 1024 in this embodiment. In step S1002, the wavelength λ of each light ray incident on each pixel is calibrated based on the pixel index $P_n(\lambda)$ of the specific pixel n as Equation (7). The deflection angle θ is derived as a function of the calibrated wavelength λ from Equations (5) and (6) in step S1003. The azimuth angle ϕ can be derived based on the rotation angle of the probe presented in Equation (4) in step S1004. In step S1005, the deflection angle θ and the azimuth angle ϕ obtained in steps S1003 and S1004 is applied to Equations (1) and (2) to derive the interception point P'(x,y,z). The image of the target object presented in the coordinate with reference to the probe is thus obtained. For the perspective view application, the function ƒ(x,y,z) of the projection plane P' is predetermined and is not related to the target object to be image and inspected. If the projection surface P' is a planar surface, a perspective view can be generated. If the projection surface is a general surface, other views including the fisheye view can be simulated. The different types of views can be generated by adjusting the distance and angle with respect to the probe 30 as shown in FIG. 1. For a general surface, more steps to project the three-dimensional surface to a two-dimensional plane are required as shown in FIG. 10. The image data is then converted and presented in the coordinate system with reference to the projection plane P' as Equation (7) in step S1006. The image data presented in the coordinate system with reference to the projection plane are then resampled by interpolation or extrapolation for proper display in step S1007.

Figure 11:
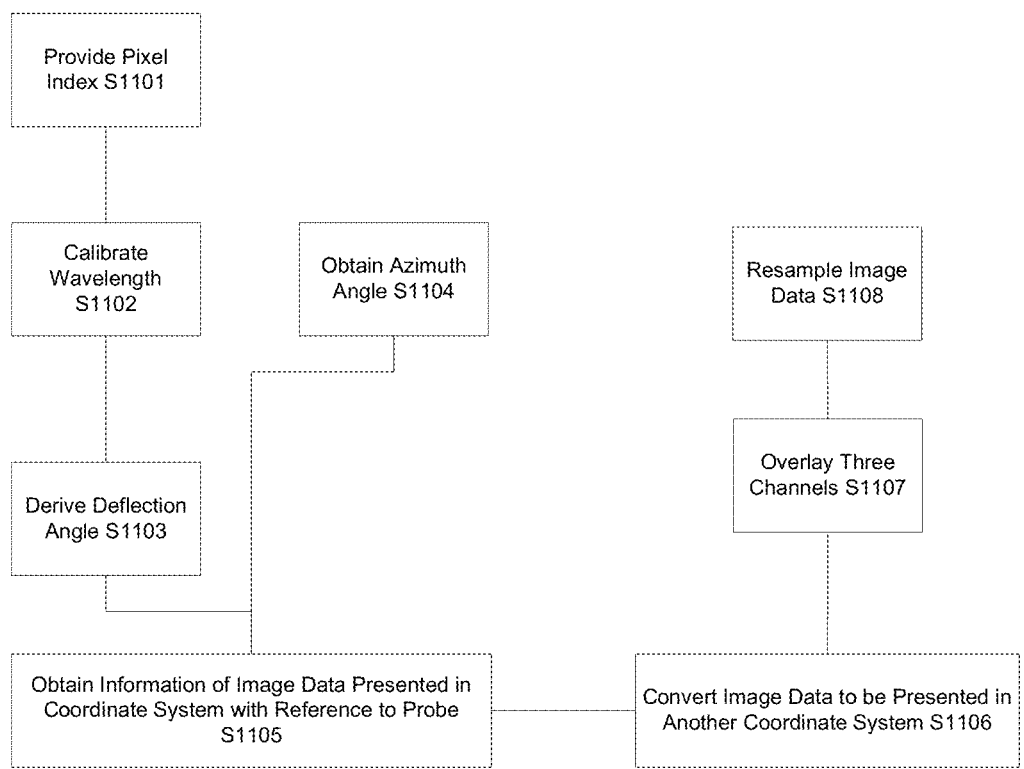
FIG. 11 is a flow chart of the color registration process.

Image registration is a process of transforming different sets of data into one coordinate system. In one embodiment, the SEE image rectification discussed above is the first step for the color image registration. Once the image for an individual color, that is, an individual channel image, is properly rectified, three or more of the channel images on the same plane are mapped and overlay with each other. Steps S1101 to S1106 are the same as steps S1001 to S1004. However, as shown FIG. 11, the steps S1101 to S1106 are repeated for three different channels, for example, for $\lambda_R$, $\lambda_G$, $\lambda_B$ for red, green, and blue colors. Each of these three channel images are then converted and presented in the new coordinate with reference to the target or projection planes. The image data for these three channels are then overlaid in step S1107 and the overlay result is then resampled by interpolation or extrapolation with three grayscale values for red (R), green (G), and blue (B) channels for each pixel in step S1108. Similarly, perspective view and fisheye view application can be generated, respectively.

The above embodiments describe the transformation of two Cartesian coordinate systems ($\vec{x}$, $\vec{y}$, $\vec{z}$) and ($\vec{\alpha}$, $\vec{\beta}$, $\vec{\gamma}$). These coordinate system in general can be Affine coordinate systems. In geometry, an Affine transformation is a function between Affine spaces which preserves points, straight lines, and planes. Sets of parallel lines remain parallel after an Affine transformation. An Affine transformation does not necessarily preserve angles between lines or distances between points, though it does preserve ratios of distances between points lying on a straight line. For many purposes an Affine space can be thought of as Euclidean space, though the concept of Affine space is far more general. That is, all Euclidean spaces are Affine, but there are Affine spaces that are non-Euclidean. In an Affine coordinate system, each output coordinate of an Affine map is a linear function of all inputs coordinates. Another way to deal with Affine transformations systematically is to select a point as the origin, and then any Affine transformation is equivalent to a linear transformation (of position vectors) followed by a translation. The linear transformations discussed above can be naturally extended to Affine coordinate systems and displayed in Affine coordinate systems. However, the transformation matrix C in Equation (9) will no longer be an orthogonal matrix if the coordinate systems are not Cartesian.

While the above disclosure describes certain illustrative embodiments, the invention is not limited to the above-described embodiments, and the following claims include various modifications and equivalent arrangements within their scope.

What is claimed is:

1. An image processing method, comprising:
   projecting at least one light ray from a probe, wherein the light ray is presented by a vector in a first affine coordinate system with a tip of the probe as an origin;
   intercepting the light ray with a projection surface, the projection surface satisfying a function in the first affine coordinate;
   obtaining a distance between the tip of the probe and an interception point of the light ray on the projection surface based on a rotation angle of the probe, a wavelength of the light ray, and a deflection angle of the light ray from the probe;
   obtaining a relationship between the first coordinate and a second affine coordinate system, the second coordinate system being defined with the projection surface as a reference;
   acquiring image data from the light ray reflected from the projection surface presented in the first affine coordinate;
   converting the image data presented in the first affine coordinate into image data presented in the second affine coordinate; and
   resampling the image data in the second coordinate system by interpolating or extrapolating a gray scale.

2. The method according to claim 1, wherein the first coordinate includes a Cartesian coordinate including an x-axis, a y-axis, and a z-axis extending along the probe.

3. The method according to claim 2, wherein the vector of the light ray is presented as:

$$\begin{cases} x = r\sin\theta\cos\varphi \\ y = r\sin\theta\sin\varphi \\ z = r\cos\theta \end{cases},$$

where r is the length of the light ray, θ is the deflection angle of the light ray, and ϕ is an azimuth angle of the light ray.

4. The method according to claim 1, wherein the function of the projection surface satisfies:
   ƒ(x, y, z)=0 at the interception point between the light ray and the projection surface.

5. The method according to claim 1, further comprising determining the azimuth angle ϕ based on a series of rotation angles of the probe with respect to scanning time between the rotation angles in a calibration or mapping process.

6. The method according to claim 1, further comprising determining the wavelength of the light ray λ based on interpolation or extrapolation from at least two distinct wavelengths and pixel indices of two pixels configured to receive the reflected light ray corresponding to the two wavelengths.

7. The method according to claim 1, further comprising determining the deflection angle θ based on the wavelength of the light ray λ, the light incident angle on the grating, the diffractin order, the grating constant, and refractive indices at two opposing sides of the grating.

8. The method according to claim 1, wherein the second affine coordinate includes a Cartesian coordinate system.

9. The method according to claim 1, wherein the projection surface includes a target surface to be imaged and analyzed.

10. The method according to claim 1, wherein the projection surface is separate from a target surface to be imaged and analyzed.

11. The method according to claim 10, wherein the projection surface includes a conjugate plane of a hypothetical image plane of the target surface to be imaged and analyzed.

12. The method according to claim 10, further comprising interpolating or resampling a grayscale value to the image data presented in the second affine coordinate.

13. The method according to claim 1, further comprising projecting a plurality of light rays from the probe.

14. The method according to claim 1, wherein the projection surface is separate from a target surface to be imaged and analyzed.

15. The method according to claim 14, wherein the projection surface includes a conjugate plane of a hypothetical image plane of the target surface to be imaged and analyzed.

16. An image processing method, comprising:
a) projecting at least one light ray of a first color from a probe, wherein the light ray is presented by a vector in a first affine coordinate system with a tip of the probe as an origin;
b) intercepting the light ray with a projection surface, the projection surface satisfying a function in the first affine coordinate;
c) obtaining a distance between the tip of the probe and an interception point of the light ray and the projection surface based on a rotation angle of the probe, a wavelength of the light ray, and a deflection angle of the light ray from the probe;
d) obtaining a relationship between the first coordinate and a second affine coordinate system, the second coordinate system being defined with the projection surface as a reference;
e) acquiring image data from the light ray reflected from the projection surface presented in the first affine coordinate;
f) converting the image data presented in the first affine coordinate into image data presented in the second affine coordinate;
g) repeating steps a) to f) for a light ray of second and third colors;
h) overlaying the image data acquired from the light rays of the first, second, and third colors; and
i) resampling the overlaid image by interpolating or extrapolating the image data presented in the second affine coordinate.

17. The method according to claim 16, wherein the first coordinate includes a Cartesian coordinate including an x-axis, a y-axis, and a z-axis extending along the probe.

18. The method according to claim 17, wherein the vector of the light ray is presented as:

$$\begin{cases} x = r\sin\theta\cos\varphi \\ y = r\sin\theta\sin\varphi \\ z = r\cos\theta \end{cases},$$

where r is the length of the light ray, θ is the deflection angle of the light ray, and φ is an azimuth angle of the light ray.

19. The method according to claim 17, wherein the function of the target surface satisfies:
$f(x, y, z)=0$ at the interception point between the light ray and the projection surface.

20. The method according to claim 17, further comprising determining the azimuth angle φ based on a series of rotation angles of the probe with respect to scanning time between the rotation angles in a calibration or mapping process.

21. The method according to claim 17, further comprising determining the wavelength of the light ray λ based on interpolation or extrapolation from at least two distinct wavelengths and pixel indices of two pixel configured to receive the reflected light ray corresponding to the two wavelengths.

22. The method according to claim 17, further comprising determining the deflection angle θ based on the wavelength of the light ray λ, the light incident angle on the grating, the diffractin order, the grating constant, and refractive indices at two opposing sides of the grating.

23. The method according to claim 17, wherein the second affine coordinate includes a Cartesian coordinate.

24. The method according to claim 17, wherein the projection surface includes a target surface to be imaged and analyzed.

25. The method according to claim 17, further comprising projecting a plurality of light rays from the probe.

26. The method according to claim 17, further comprising interpolating or resampling a grayscale value to the image data presented in the second affine coordinate.

27. A spectrally encoded endoscopic apparatus, comprising:
a light source;
a probe having a proximal end optically coupled to the light source and a distal end;
a grating attached to the distal end; and
a spectrometer, wherein:
the light source is configured to generate a light propagating through the grating and then projecting on a projection surface, and
the spectrometer is configured to
receive the light reflected from the projection surface;
obtain three-dimensional information of image data carried by the reflected light presented in a first coordinate system with reference to the probe based on a rotation angle of the probe, a wavelength of the light, and a deflection angle of the light deflecting from the probe;
transform the location information of the image data from the first coordinate system into a second coordinate system with reference to the projection surface; and
resample the image data by interpolating or extrapolating a grayscale value.

28. The apparatus according to claim 27, further comprising a motor configured to rotate the probe.

29. The apparatus according to claim 27, further comprising a processor and/or an encoder configured to control and calibrate the motor, so as to determine the rotation angle of the probe.

30. The apparatus according to claim 27, wherein the projection surface includes a target surface to be imaged and analyzed by the spectrometer.

31. The apparatus according to claim 27, wherein the projection surface is separate from a target surface to be imaged and analyzed by the spectrometer.

32. The apparatus according to claim 31, wherein the spectrometer is further configured to generate a perspective view or a fisheye view of the image data in accordance with an angle and a distance of the projection surface with respect to the probe.

\* \* \* \* \*